United States Patent [19]

Haggar

[11] 4,278,437

[45] Jul. 14, 1981

[54] FLUID SPECIMEN HOLDER FOR BIOLOGICAL FLUID TESTING

[76] Inventor: Jan Haggar, 7056 Little Harbor, Huntington Beach, Calif. 92648

[21] Appl. No.: 28,545

[22] Filed: Apr. 9, 1979

[51] Int. Cl.[3] ..................... G01N 33/48; G01N 31/00; G01N 33/16; B01L 3/00

[52] U.S. Cl. ................................... 23/230 B; 73/64.1; 233/26; 233/1 A; 128/764; 422/73; 422/102; 356/246

[58] Field of Search ............... 233/1 A, 26; 23/230 B; 73/64.1; 422/73, 102, 99; 366/210, 211; 356/39, 427, 246; 250/576; D9/54–56; 128/760, 763, 764; 435/296

[56] References Cited

U.S. PATENT DOCUMENTS

| | | | |
|---|---|---|---|
| D. 4170 | 6/1870 | Rose | D9/54 |
| 3,607,098 | 9/1971 | Strande | 422/102 |
| 3,684,453 | 8/1972 | Lartigue et al. | 356/246 |
| 3,702,806 | 11/1972 | Oliva | 435/296 |

OTHER PUBLICATIONS

*Corning,* Corning Glass Works, N.Y., 1971, pp. 203, 27.

*Primary Examiner*—William F. Smith
*Assistant Examiner*—Chris Konkol
*Attorney, Agent, or Firm*—Gary Appel

[57] ABSTRACT

A fluid, for example, blood, specimen holder for biological testing comprises an elongate transparent tube of equilateral triangle cross section. The intersection region of two sides of the tube forms a channel for controlling, channelling, and concentrating flow of a fluid specimen as the tube is agitated to flow the fluid specimen back and forth between ends of the tube during biological fluid testing. The third side of the tube opposite the fluid flow channel provides a flat impinging surface for a light source used in determining translucency characteristics. A removable end cap for the tube is formed having a small diameter inner portion which projects into the tube when the cap is installed thereon. A transverse diaphragm provided at the inner end of the inner portion enables the cap to be penetrated by a hypodermic needle for introducing a fluid specimen into the tube. The projecting inner portion is configured for preventing escape of fluid from the tube during biological testing. A filling index mark is provided near the closed end of the tube to enable a tube to be filled to a predetermined level a corresponding method for testing fluid specimens is also provided.

3 Claims, 6 Drawing Figures

FLUID SPECIMEN HOLDER FOR BIOLOGICAL FLUID TESTING

BACKGROUND OF THE INVENTION

Field of the Invention

The present invention relates generally to the field of apparatus for biological laboratory sample testing and more particularly to biological fluid specimen test tubes for use with such apparatus.

For numerous medical purposes, measurement of the rate at which a patient's blood coagulates or clots is necessary. One of these purposes relates, as an example, to kidney dialysis or blood cleansing treatments for patients having kidney problems. During subsequent treatments, and perhaps more than once in the course of a single treatment, measurement of the rate at which the patient's blood coagulates is essential to establishing or adjusting treatment parameters.

Typically, blood coagulation rate or the time required to reach a predetermined degree of coagulation is determined by subjecting a small specimen of the patient's blood to a coagulation test. In such a test, a vial or small test tube containing the blood specimen, together generally, with small quantities of selected additives such as siliceous Earth, is agitated in some manner while consistence of the blood in the specimen holder is monitored for coagulation.

Frequently, the monitoring is done automatically using a light source on one side of a transparent blood specimen holder and a light sensitive photo detector on an opposite side of the holder. As the blood specimen thickens and coagulates, its light transmitting characteristics are reduced. Thus, when light transmitted through the blood specimen, as detected by the photosensor, falls to a level corresponding to a preselected extent of coagulation as previously determined by suitable system calibration, the photosensor may be used to automatically trigger stop a timer, which was started when coagulation test started.

As can readily be appreciated, very precise and accurate coagulation rate determinations are often critical to a patient's life. A high degree of precision and accuracy is particularly necessary when monitoring for slight changes in a patient's blood coagulation rate as is often the situation.

Heretofore, the necessary precision and accuracy in determining blood specimen coagulation rate or time to coagulate has been difficult if not generally impossible to achieve, even when the tests have been performed with great care. To a large extent, this lack of precision and accuracy has been caused by the manner in which the blood specimen has been contained during the coagulation tests. Typically, small cylindrical test tubes of the type and configuration commonly used in chemical laboratories have been used to hold the blood specimen. As a result, when the tube is agitated, usually by rocking or tilting a horizontally oriented tube up and down so that the blood specimen runs back and forth between ends of the tube, the blood tends to "wash" around inside the tube in a sufficiently uncontrolled manner that transmission of coagulation selecting light is affected. Also, since the tube is round in cross section, light shining downwardly through the tube from an external source towards a photosensor tends to be diffused and reflected in a difficult to predict manner. Degree of translucency is a critical parameter for determining coagulation time.

As a result of blood specimen movement around the inside of the specimen holding tube, and depression and reflection of light from the light source as the tube is rocked to induce coagulation, erroneous light readings are often made by the photosensor. That is, at certain positions of the specimen tube and for certain uncontrolled movement of the blood, light reading of the photosensor may indicate the desired degree of coagulation has been reached when, in fact, such is not the case. Under other conditions, the light reading may indicate lack of coagulation after the desired degree of coagulation has already been reached.

Other problems have retarded the coagulation of the blood sample as it is introduced into the specimen holder, thereby possibly affecting coagulation rate, and difficulty in always filling the specimen holder to the same extent, or leakage of part of the specimen from the holder, thereby changing light transmission characteristics of the sample because of translucency variation.

Because of these and other problems with blood specimen holders for coagulation tests, applicant has invented a special specimen holder which overcomes many, if not all, of these problems.

SUMMARY OF THE INVENTION

A fluid specimen holder according to the present invention, for use in blood coagulation testing, comprises an elongate, transparent specimen tube having a closed end and an open end. The tube is formed having a flat side extending for a substantial length thereof; in opposition thereto are means defining a blood specimen flow channel for limiting side flow of a blood specimen contained in the tube as the tube is rocked to alternately raise and lower opposite ends of the tube during coagulation testing. The flat side is constructed to be several times wider than the blood flow channel for ease in illumination of the blood specimen to determine when coagulation has occurred. A removable cap is provided for sealing the open end of the tube.

More specifically, the tube is formed triangular in cross section with first, second and third flat sides, the means defining the blood flow channel including intersecting regions of the first and second sides and the mentioned flat side opposite the channel comprising the third side.

The end cap is formed having a central portion which projects into the tube when the cap is installed in the tube to close the open end. The diameter of the central portion is substantially less than that of the open end of the tube to permit blood to flow around such central portion when the tube containing a blood specimen is tilted with the open tube end downwardly.

A transverse diaphragm formed in the cap projecting portion is adapted for piercing by the needle of a hypodermic syringe to enable a blood sample to be introduced into the tube with the tube closed by the end cap. The inwardly projection portion of the cap prevents blood from escaping during specimen agitation through a hole made by the syringe needle in the diaphragm.

An index mark on the tube enables a preselected amount of blood to be introduced into the specimen holder.

Because of the flat side of the tube opposite the blood flow channel, light from an external source incident in the tube is not reflected or diffused in an uncontrolled manner as is the situation when a conventional, cylindrical test tube is used as a specimen holder. Consequently more precise and accurate blood coagulation measurements are made possible by focusing rather than diffusing light impingement.

A corresponding method for fluid specimen testing comprises the steps of forming an at least one partially transparent test specimen holding tube having a polyhedral cross section with at least first, second and third sides, the third side being transparent and opposite to an intersection between the first and second sides, installing a pierceable end upon the holding tube and injecting a fluid specimen to be tested into the tube through the end cap by means of a hypodermic needle. Included are the steps of orienting the tube so that the intersection between the first and second sides forms a fluid specimen flow channel, rocking the tube about a transverse axis so that the specimen flows back and forth in said flow channel and monitoring the specimen through said third side. The method further forming the end cap to retain the fluid in the tube and illuminating the specimen, during rocking and monitoring, from an external source.

BRIEF DESCRIPTION OF THE DRAWINGS

A better understanding of the present invention may be had from a consideration of the following detailed description, taken in conjunction with the accompanying drawings in which.

DESCRIPTION OF THE PREFERRED EMBODIMENT

Figure 1:
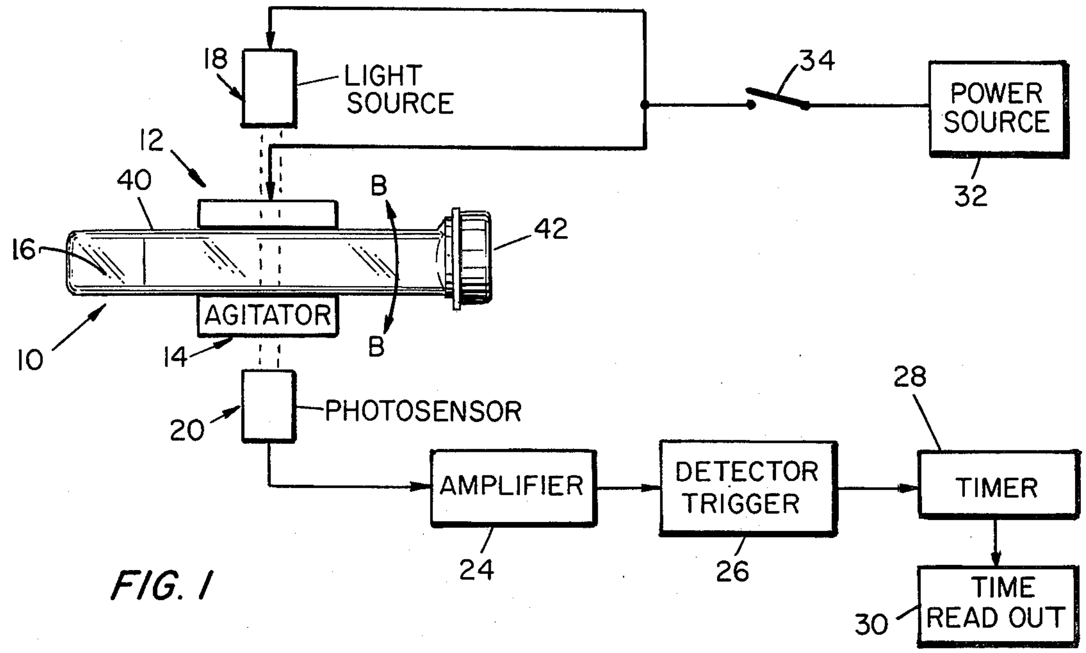
FIG. 1 is a schematic drawing showing a blood specimen holder according to the present invention as used in a blood coagulation testing system.

Shown in FIG. 1 is a transparent blood (or other biological fluid) specimen holder 10, in accordance with the present invention, as may be used in an exemplary blood coagulation testing or timing system 12. Included, for illustrative purposes, in the system 12 is an agitator 14 which holds and rocks the specimen holder 10 in the direction of arrows B-B. Determination of coagulation time or rate of a blood (or other translucent fluid) sample 16 contained in the specimen holder 10 is by means of a light source 18 which shines light through the specimen holder and blood sample therein towards a conventional light detector or photosensor 20.

Electric signals from the photosensor 20 are fed through an amplifier 24 to a detecter/trigger 26 and thence to a timer 28. Output from the timer 28 is fed to a conventional timer readout 30. Power is provided to the light source 18 and agitator 14 by a power source 32 and is controlled by a switch 34.

In operation, when the light source 18 and agitator 14 are energized by closing the switch 34, rocking of the specimen holder 10 starts. The photosensor 20 picks up light from the source 18 shining through the holder 10 and the blood sample 16 contained therein and the timer 28 is started. The timer 28 keeps running until light received by the photosensor 20 falls, due to coagulation of the blood 16 in the holder 10, below a preselected level corresponding to a preselected or calibrated degree of blood coagulation. At that instant, the timer 28 is triggered off by the detector/trigger 26 and the length of time taken for the coagulation process is displayed on the readout 30. The agitator 14 may be stopped periodically for a sufficient time to enable the photosensor readings to be made.

Figure 2:
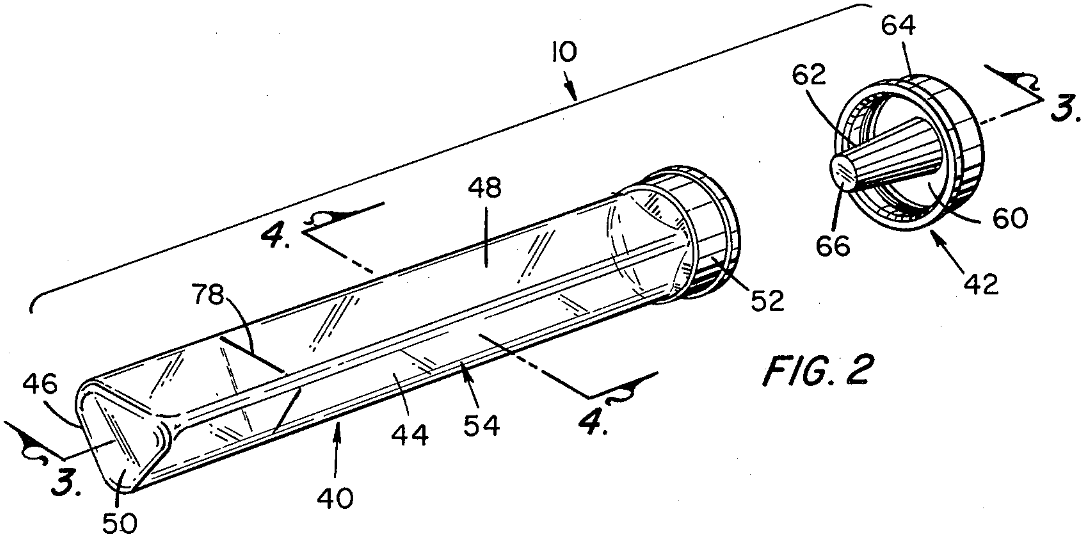
FIG. 2 is an exploded perspective drawing showing tube and end cap portions of the blood specimen holder.
Figure 3:
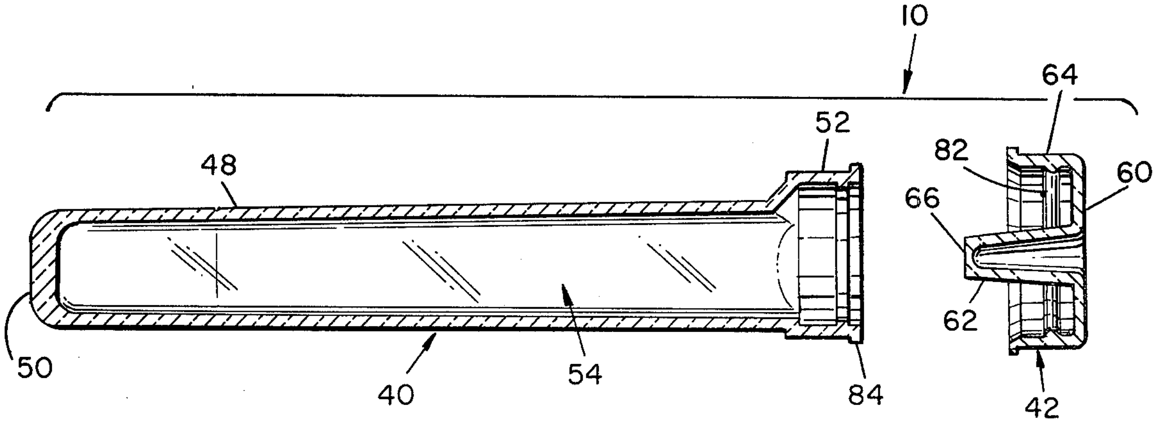
FIG. 3 is a vertical sectional view taken along line 3—3 of FIG. 2, showing features of the tube and end cap.
Figure 4:
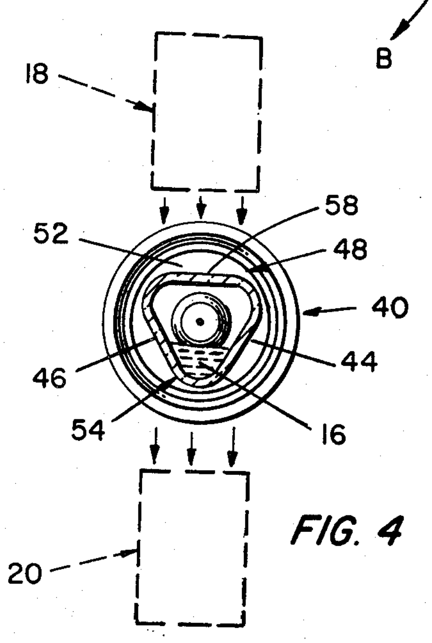
FIG. 4 is a transverse sectional view taken along line 4—4 of FIG. 2, showing the triangular cross-section of the tube.

More specifically, the specimen holder 10, as best seen in FIGS. 2–4, comprises a transparent vial or tube 40, which is open at one end, and an end cap or cover 42 which is detachably received into the tube to close the open end thereof.

The tube 40 is formed having first, second and third flat sides 44, 46 and 48, respectively, which extend a substantial length of the tube 40 from a closed end 50 to a cylindrical cap receiving portion 52 at the open end. Abutting edges of the sides 44, 46 and 48 are formed so the tube 40 is triangular in cross-section (FIG. 4). Preferably all three sides 44, 46 and 48 are equal in width so that the triangular cross-section is equilateral in shape. However, at least the first and second sides 44 and 46 should be equal in width.

With the tube 40 oriented (on its side) with the third flat side 48 uppermost, corresponding to the orientation of the specimen holder 10 in the agitator 14 (FIG. 1), a "V"-shaped blood flow channel or trough 54 is formed along the lower side of the tube 40 intersection of adjacent portions of the two sides 44 and 46.

As seen in phantom lines in FIG. 4, when the specimen holder 10 is in use in the agitator 14, the blood sample 16 is confined to this trough region 54, with an upper surface 56 of the blood sample being parallel to, when the tube 40 is horizontal to an upper surface 58 of the side 48, thus enabling optimum transmission of light from the source 18 through the tube 40 and blood sample 16 to the photosensor 20. As can be seen, width of the side 48 opposite the channel 54 is substantially wider than the diamond as defined by the blood specimen 16 contained therein.

Since light from the source 18 falls normally onto the upper surface 58, light scattering and diffraction are minimized. This importantly enables precise, accurate time measurements because the same amount of light is always focally transmitted to blood samples 16 in the tube 40 whenever one of the holders 10 is used in the system 12.

It is to be appreciated that the tube 40 could alternatively, for example, be made five-sided instead of three-sided, with most of the same advantages mentioned, so long as one flat surface was directly opposite to a blood flow trough formed between an adjacent pair of sides.

Retention of the blood sample 16 in the tube 40 is provided by the end cap 42. Although almost any type of end cap or plug could be used for such purpose, including a small carls stopper fitting inside the end portion 52, the particular end cap 52 illustrated has important and very useful features and advantages.

Comprising the cap 52 are a circular end piece 60 which, in a central region, is formed to project inwardly (inside the tube 40 upon assembly) to form an elongated tubular projecting portion 62 having a diameter substantially smaller than outer diameter of the end piece. For example, the end piece outer diameter may be 3 or 4 times the outer diameter of the projection portion 62. Length of the projecting portion 62 may be about twice the length (width) of a flange or edge portion 64 which is joined to the end piece 60 at an outer periphery thereof.

Figure 6:
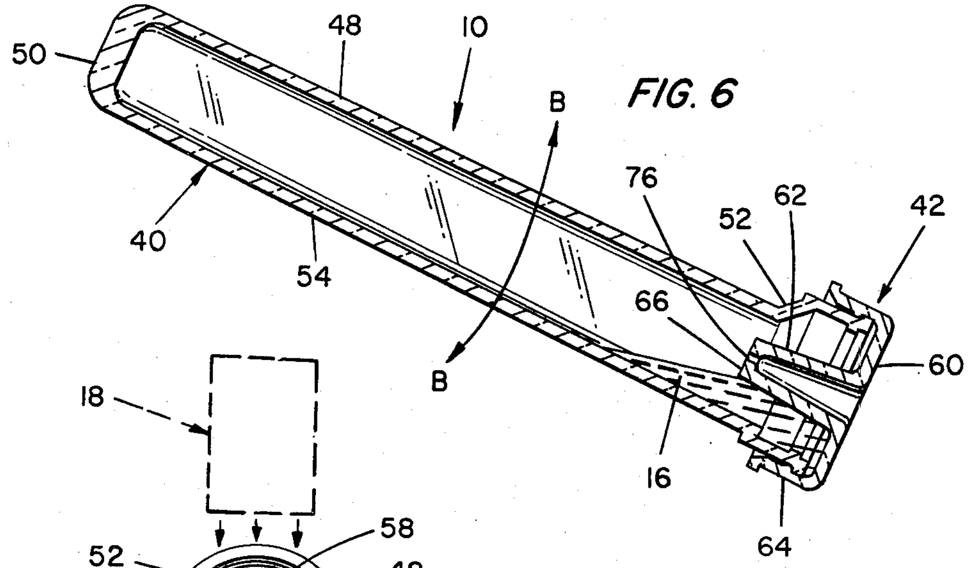
FIG. 6 is a vertical cross-sectional view of the specimen holder showing blood specimen containment during agitation.

The innermost end of the projecting cap portion 62 is closed by a transverse diaphragm or membrance 66 which is adapted for being easily, pierced by a hypodermic needle 68 associated with a blood sample syringe 70 (FIG. 5) for introducing blood into the holder 10. Because of the smaller outside diameter of the projecting portion 62 and the inwardly extending length thereof, a small opening 76 in the diaphragm 66 (FIG. 6), caused by piercing of the needle 68 when a blood sample is introduced into the holder 10, is always above the blood specimen 16 when the holder is agitated or rocked to a position in which the cap 42 is lower than the tube end 50. Consequently none of the blood specimen 16 runs out of the opening 76 to reduce the blood volume of the specimen and to contaminate portions of the system 12.

It is important to be able to introduce the blood specimen 16 into the holder 10 without opening the holder since small quantities of additive materials, such as Siliceous Earth, are required to be in the holder for mixing with the blood for coagulation testing. Since the blood specimen 16 can be introduced into the holder 10 with the cap 42 on the tube, measured quantities of required materials can be preloaded into the holders without change of any subsequent loss. For precise, accurate and consistent results, exact quantities of such additive materials must be used. Loss of any part of these materials can substantially effect coagulation measurements.

Similarly, after a measured quantity of blood has been introduced into the closed holder 10 by the syringe 70, for example, by filling the tube 40 to an index mark 78 proximate the tube end 50 (FIG. 2) when the tube is vertical, it is essential to accurate, precise coagulation measurements that none of the blood be lost during the agitation process. If some of the blood is lost, light transmission through the specimen 16 will tend to be greater; as a result, the timer 28 may not be triggered off at the correct time and coagulation time will appear to be greater than it actually is.

Material used for the tube 40 may be glass or any medical grade or type of transparent plastic. The cap 42 is made of a resilient plastic, which is sufficiently elastic to enable tight fitting over the tube end region 52, so as to form a leak proof seal. To enhance such sealing and to retain the cap 42 on the tube, a small annular ridge 82 is formed in an inner surface of the end cap adjacent to the end piece 60 (FIG. 3). A correspondenting outer annular ridge 84, over which the cap ridge 82 slips for locking, is formed around the tube end region 52 adjacent the open end.

For purposes of economy, since the possibility of contamination exists, the holder 10 is constructed sufficiently inexpensively to be discardable after a single use.

Figure 5:
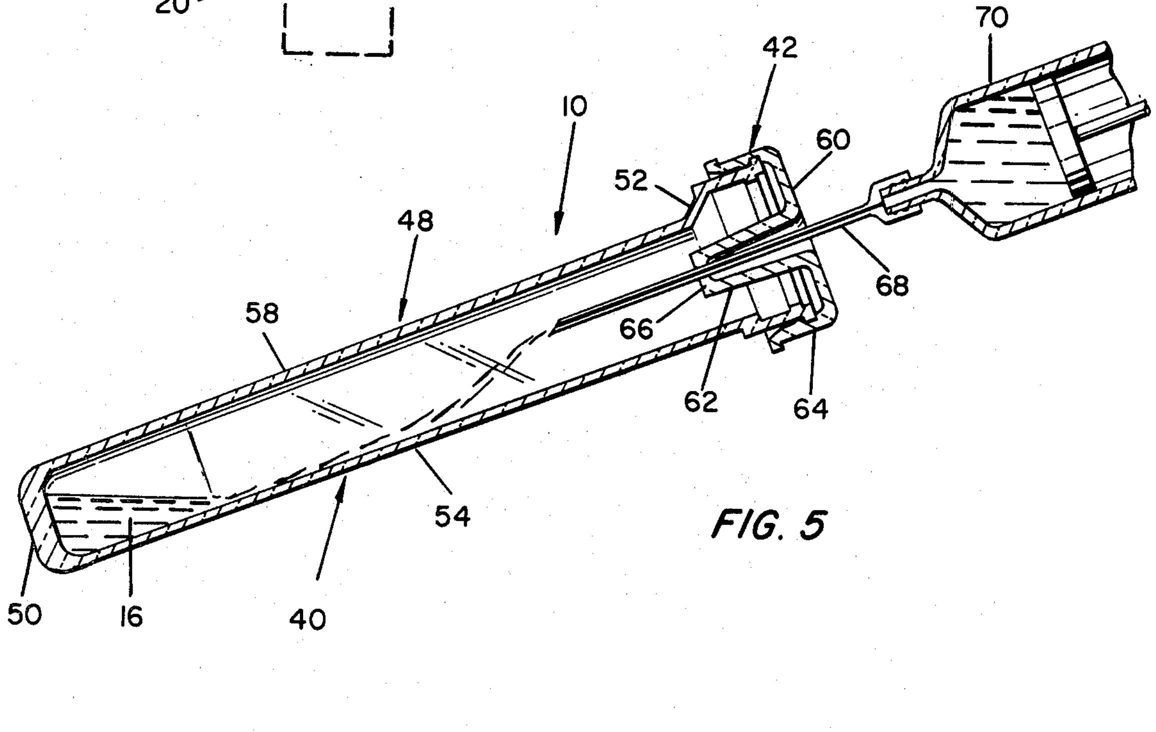
FIG. 5 is a perspective view of the specimen holder showing filling thereof by a hypodermic needle.

Use of the specimen holder 10 is generally apparent from the above description and from FIG. 5 which shows the manner in which the holder is filled with a blood sample, and FIG. 1 which shows relationship of the specimen holder and the rest of a coagulation testing system 12. FIG. 4 illustrates the light path through the tube 40 and blood specimen 16 contained therein, light being shown against the tube upper surface 58 by the light source and being picked up by the light sensor 20 after passing through the tube 40 and blood specimen 16. FIG. 4 shows that the blood specimen 16 is concentrated with a triangular cross-section determined by the tube sides 44 and 48 in the trough region 54. It is apparent that because of the relatively steep sides of the trough region 54, movement of the blood specimen 16 is limited to longitudinal movement in the trough region and washing or splashing of the blood specimen around sides of the tube 40 is minimized.

Although there has been described above a specific arrangement of a blood specimen holder for coagulation testing, in accordance with the invention for purposes of illustrating the manner in which the invention may be used to advantage, it will be appreciated that the invention is not limited thereto and has application in other types of blood and biological fluid testing. Accordingly, any and all modifications, variations or equivalent arrangements which may occur to those skilled in the art should be considered to be within the scope of the invention as defined in the appended claims.

What is claimed is:

1. A fluid specimen holder for a biological fluid test apparatus, which comprises:

(a) an elongate, transparent specimen tube, having a closed end and an open end, said tube being formed having a generally polyhedral cross section with at least first, second and third sides, the intersecting region of the first and second sides defining a fluid specimen flow channel for limiting side flow of a fluid specimen contained in the tube when the tube is rocked to alternately raise and lower opposite ends thereof during specimen testing, said third side being formed having a flat width several times greater than that of said channel; and (b) a removable end cap for closing the open end of the tube, said end cap being formed having a generally tubular central portion including a transverse diaphragm having a thickness easily pierced by a hypodermic needle to enable introduction of a fluid sample into the closed tube, said central portion being formed having a cross-sectional diameter no more than about one third the corresponding cross-sectional diameter of the tube and having a length which is at least about twice the length of the edge portion of the cap, thereby providing containment of the fluid specimen in the tube when the tube is rocked and the specimen introduced into the tube comes into contact with the cap.

2. The fluid specimen holder according to claim 1, wherein said tube includes means defining a filling index mark proximate said closed end, said mark indicating the amount of fluid to be introduced into said tube for translucency sensitivity testing.

3. A method for fluid specimen testing, which comprises the steps of:

(a) forming an at least one partially transparent fluid test specimen holding tube having a polyhedral cross-section with at least first, second nd third sides with said third side being transparent and being opposite an intersection between said first and second sides;

(b) installing a pierceable end cap into the specimen holding tube, including forming the cap having an inner axially projecting portion which has a diameter of less than about one third of a corresponding tube diameter and which extends into the tube a distance of at least about twice a length of a cap retaining flange;

(c) injecting a fluid specimen into the holding tube through said end cap by means of a hypodermic needle;

(d) orienting the holding tube so that the intersection between the first and second tube sides forms a flow channel for the introduced fluid specimen;

(e) rocking the tube about a transverse axis so that the fluid specimen flows back and forth in the flow channel defined by the intersection of the tube first and second sides; and, (f) monitoring the specimen through the third tube side as the tube is rocked about the transverse axis.

* * * * *